United States Patent [19]

Cross et al.

[11] 4,217,357
[45] Aug. 12, 1980

[54] INHIBITION OF THROMBOXANE SYNTHETASE WITH 3-(IMIDAZOL-1-YLALKYL)INDOLES

[75] Inventors: Peter E. Cross, Canterbury; Roger P. Dickinson, Dover, both of England

[73] Assignee: Pfizer Inc., New York, N.Y.

[21] Appl. No.: 14,217

[22] Filed: Feb. 22, 1979

[30] Foreign Application Priority Data

Feb. 24, 1978 [GB] United Kingdom ................. 7400/78

[51] Int. Cl.² .................. A61K 31/415; C07D 403/06
[52] U.S. Cl. .................................. 424/273 R; 548/336
[58] Field of Search ...................... 548/336; 424/273 R

[56] References Cited

U.S. PATENT DOCUMENTS 3,931,229    1/1976    Zinnes et al. ..................... 548/336

OTHER PUBLICATIONS

Andreani et al., J. Chem. Soc. (London) C, 1970, pp. 1157–1161.
Decodts et al., C. R. Acad. Sci., Paris, Ser. C, 1968, vol. 266, pp. 1168–1170.

*Primary Examiner*—Henry R. Jiles
*Assistant Examiner*—Richard A. Schwartz
*Attorney, Agent, or Firm*—Connolly and Hutz

[57] ABSTRACT

A series of unsubstituted and substituted 3-(imidazol-1-ylalkyl)indole compounds has been prepared by reacting the appropriately substituted 3-methylindole starting material with imidazole per se, followed by further reaction with a proper acylating or alkylating agent of choice, if so desired. The resulting indole derivatives are useful in therapy for the treatment at ischaemic heart disease, migraine, transient ischaemic attack and stroke. Typical members include such preferred compounds as 3-(imidazol-1-ylmethyl)-1-methylindole and 3-(imidazol-1-ylmethyl)-2-isopropylindole, respectively.

30 Claims, No Drawings

INHIBITION OF THROMBOXANE SYNTHETASE WITH 3-(IMIDAZOL-1-YLALKYL)INDOLES

BACKGROUND OF THE INVENTION

This invention relates to certain indole derivatives, specifically, to certain 3-(imidazol-1-ylalkyl)indoles, and to their use in selectively inhibiting the action of the thromboxane synthetase enzyme, i.e., without significantly inhibiting the action of the prostacyclin synthetase or cyclo-oxygenase enzymes. The compounds are therefore useful, for example, in the treatment of ischaemic heart disease, stroke, transient ischaemic attack and migraine.

SUMMARY OF THE INVENTION

Thus, according to the invention, there is provided an organic base compound of the formula:

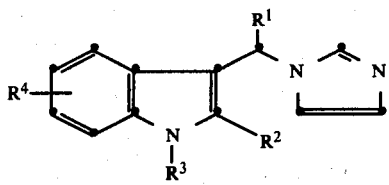

and the pharmaceutically acceptable acid addition salts thereof, wherein $R^1$ is hydrogen or lower alkyl; $R^2$ is hydrogen, lower alkyl, lower cycloalkyl, adamantyl, or a phenyl or benzyl group in which the phenyl moiety is unsubstituted on the ring or is monosubstituted with halogen, hydroxy, lower alkyl, lower alkoxy or trifluoromethyl; $R^3$ is hydrogen, lower alkyl, allyl, 3-methylallyl, lower cycloalkylmethyl, lower cycloalkylethyl, lower alkoxy-lower alkyl, di(lower alkyl)aminolower alkyl, lower alkanoyl, lower cycloalkylcarbonyl, or a benzyl or benzoyl group in which the phenyl moiety is unsubstituted on the ring or is monosubstituted with halogen, hydroxy, lower alkyl, lower alkoxy or trifluoromethyl; and $R^4$ is hydrogen, lower alkyl, lower alkoxy, halogen, hydroxy, trifluoromethyl, di(lower alkyl)amino or a benzyloxy group in which the phenyl moiety is unsubstituted on the ring or is monosubstituted with halogen, hydroxy, lower alkyl, lower alkoxy or trifluoromethyl; with the proviso that at least one of $R^1$, $R^2$, $R^3$ and $R^4$ is other than hydrogen.

A subgenus of compounds within the scope of the present invention includes those wherein $R^1$, $R^3$ and $R^4$ are each hydrogen and $R^3$ is lower alkyl such as isopropyl; lower cycloalkyl such as cyclopropyl or cyclohexyl; benzyl; halophenyl such as o-chlorophenyl; and tolyl. A further subgenus of compounds includes those wherein $R^1$ is hydrogen or methyl, $R^2$ is hydrogen, $R^3$ is lower alkyl or allyl and $R^4$ is hydrogen. Still a further subgenus of compounds includes those wherein $R^1$, $R^2$ and $R^4$ are each hydrogen and $R^3$ is lower cycloalkylmethyl or lower alkanoyl.

In this application, the term "lower" when applied to an alkyl, alkoxy or alkanoyl group means that the group contains not more than four carbon atoms, and when applied to a cycloalkyl group means that the group contains not more than seven carbon atoms. The term "halogen" means fluorine, chlorine, bromine or iodine.

In addition, the invention provides a pharmaceutical composition comprising a compound of the formula (I) or a pharmaceutically acceptable acid addition salt thereof, together with a pharmaceutically acceptable carrier or diluent.

The preparation of the compound in which $R^1$, $R^2$, $R^3$ and $R^4$ are all hydrogen, i.e., 3-(imidazol-1-ylmethyl)-indole, has been described in Compt. Rend. Acad. Sci., Paris, Ser. C, 1968, 266 (15), 1168–80 and J. Chem. Soc. (C), 1970, 1157–1161, but no previous medical or any other use has been proposed for it.

Thus, the invention also provides a method of inhibiting the action of the thromboxane synthetase enzyme in an animal, including a human being, without significantly inhibiting the action of the prostacyclin synthetase or cyclo-oxygenase enzymes, which comprises administering said animal an effective amount of a compound of the formula (I), without proviso, or a pharmaceutically acceptable acid addition salt thereof, or a pharmaceutical composition comprising such a compound or salt together with a pharmaceutically acceptable carrier or diluent. The pharmaceutical composition is preferably in unit dosage form (as hereinafter defined).

The invention yet further provides a compound of the formula (I), without proviso, or a pharmaceutically acceptable acid addition salt thereof, or a pharmaceutical composition preferably in unit dosage form (as hereinafter defined) comprising such a compound or salt together with a pharmaceutically acceptable carrier or diluent, for use in treating an animal, including a human being, to inhibit the action of the thromboxane synthetase enzyme in said animal without significantly inhibiting the action of the prostacyclin synthetase or cyclo-oxygenase enzymes.

The invention also includes a pharmaceutical composition in unit dosage form (as hereinafter defined) comprising a compound of the formula (I), without proviso, or a pharmaceutically acceptable acid addition salt thereof, together with a pharmaceutically acceptable carrier or diluent.

By the term "unit dosage form" as used herein is meant a physically discrete unit containing an individual quantity of the active component in association with a pharmaceutically acceptable carrier or diluent, the quantity of active component being such that at least one unit or severable fraction of a unit is required for a single therapeutic administration. In the case of severable units, such as scored tablets, at least one severable fraction such as a one-half or one-quarter of the unit may be all that is required for a single therapeutic administration. It will be appreciated that the term "unit dosage form" does not include mere solutions except when the solutions are packaged in ingestible containers, e.g., soft capsules, or have been prepared so as to be suitable for parenteral administration, e.g., in vials of solution suitable for parenteral injection.

Pharmaceutically acceptable acid addition salts of the compounds of the invention are salts with acids containing pharmaceutically acceptable anions, e.g., the hydrochloride, hydrobromide, sulfate or bisulfate, phosphate or acid phosphate, acetate, maleate, fumarate, lactate, tartrate, citrate, gluconate, succinate and p-toluenesulfonate salts.

Preferred compounds of the invention are those in which (a) $R^1$ is hydrogen or methyl; (b) $R^3$ is hydrogen and $R^2$ is hydrogen, isopropyl, cyclopropyl, cyclohexyl, benzyl, o-tolyl, p-tolyl or o-chlorophenyl; (c) $R^2$ is hydrogen and $R^3$ is methyl, ethyl, n-propyl, allyl, cyclopropylmethyl, acetyl, p-methylbenzoyl or p-methoxybenzoyl; and (d) $R^4$ is hydrogen.

Where the compounds of the invention contain an asymmetric center, the invention includes the racemic mixtures and the separated D- and L- optically-active isomeric forms as all being well within its scope. These optically-active isomeric forms are, of course, readily obtainable by conventional methods, e.g., by fractional crystallization of a salt of the invention that is derived from a suitably selected optically-active acid.

DETAILED DESCRIPTION OF THE INVENTION

The compounds of the invention may be prepared by a number of routes, including the following:

(1) The compounds of the invention in which $R^3$ is hydrogen can be prepared by reacting an indole of the formula:

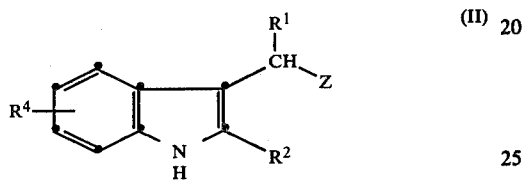

wherein $R^1$, $R^2$ and $R^4$ are as defined above and Z is a good "leaving" group, with imidazole per se. In this reaction, Z is preferably a "leaving" group such as $-N(C_1-C_4$ alkyl$)_2$, $-N^{\oplus}(C_1-C_4$ alkyl$)_3$, $-Cl$, $-Br$, $-OSO_2(C_1-C_4$ alkyl$)$, $-OSO_2$(phenyl), $-OSO_2$(tolyl) or $-OSO_2$(p-anisyl) and it is most preferably $-N(CH_3)_2$.

In a typical procedure, the compound of the formula (II) and imidazole are refluxed together in a suitable solvent, e.g., xylene, for from one to three hours. The solution is then cooled to crystallize the desired product out of solution. If necessary, petroleum ether (b.p. 60°-80° C.) may be added to induce crystallization. The final product can then be recovered by means of filtration and recrystallized from a suitable solvent.

The starting materials of formula (II) are either known compounds of else they may be prepared by using procedures analogous to those described in the prior art, e.g., as set forth below, viz., (i),

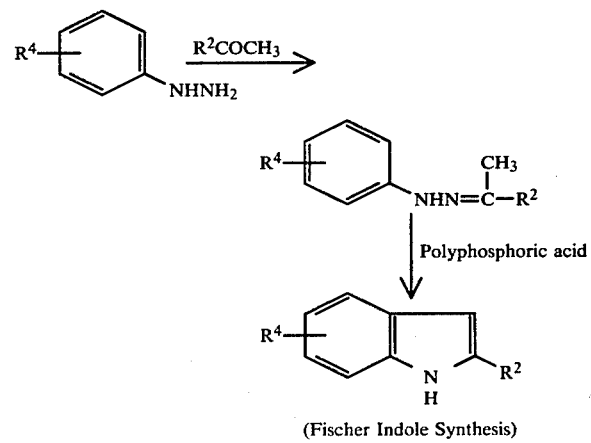

(Fischer Indole Synthesis)

or

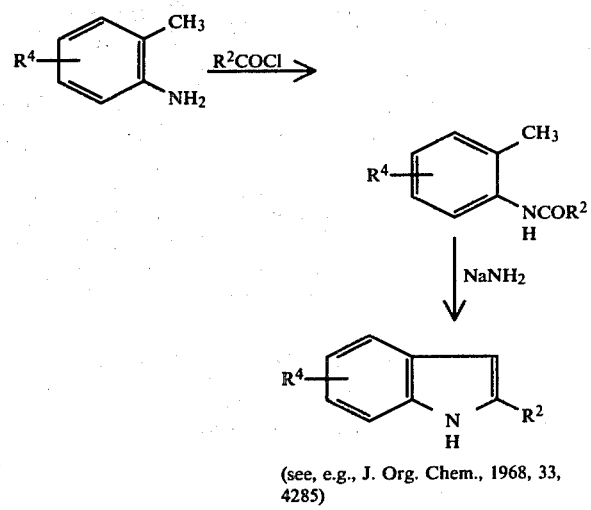

(see, e.g., J. Org. Chem., 1968, 33, 4285)

followed by, e.g., (ii),

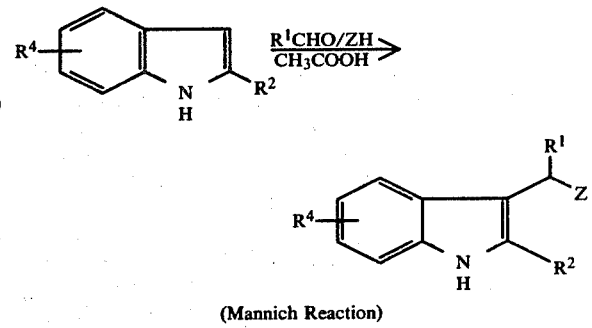

(Mannich Reaction)

wherein Z is specifically defined as $-N(C_1-C_4$ alkyl$)_2$.

Again, compounds in which Z is a "leaving" group other than $-N(C_1-C_4$ alkyl$)_2$ may be prepared by conventional procedures. For example, compounds in which Z is $-N^{\oplus}(C_1-C_4$ alkyl$)_3$ are generally prepared by alkylation of the corresponding dialkylamino derivative with an appropriate alkyl iodide, while the compounds in which Z is either $-Cl$ or $-Br$ are generally prepared by halogenation of the corresponding hydroxy compounds (which are either known compounds or else are easily synthesized by conventional methods). The compounds in which Z is $-OSO_2(C_1-C_4$ alkyl$)$ or $-OSO_2$(phenyl), $-OSO_2$(tolyl) or $-OSO_2$(p-anisyl) are also generally prepared from the corresponding hydroxy compounds, viz., by reacting them with the appropriate alkyl or aryl sulfonyl chloride of choice in the presence of an organic base.

(2) The compounds of the invention in which $R^3$ is other than hydrogen can be prepared by reacting the corresponding compound of the formula (I) in which $R^3$ is hydrogen with an appropriate alkylating or acylating agent of choice in the presence of a base, such as sodium hydride, which forms the anion:

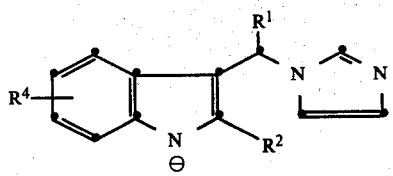

In a typical procedure, the appropriate compound of the formula (I) in which $R^3$ is hydrogen is dissolved in a suitable solvent, e.g., dry dimethylformamide, and sodium hydride is then carefully added. The appropriate alkylating or acylating agent of choice is then added next, and the resulting solution is carefully stirred at room temperature (~25° C.) for a period of up to 24 hours. The spent reaction mixture is then poured into water, and the resulting mixture extracted with a suitable solvent such as ethyl acetate, followed by separation of the two phases. The organic phase is then washed with water, dried and evaporated to give the desired product, which if necessary may be recrystallized from a suitable solvent.

Certain compounds of the invention can be prepared by conventional means from other compounds of the invention, e.g., compounds in which $R^2$ or $R^3$ contains a benzene ring substituted with a hydroxy group, or in which $R^4$ is a hydroxy group, can be prepared by demethylation or debenzylation of the corresponding methoxy and benzyloxy compounds.

The pharmaceutically acceptable acid addition salts of the compounds of the invention can be prepared by conventional procedures, e.g., by reacting the free base in a suitable solvent, such as ethanol, with a solution of the appropriate acid in a suitable solvent like diethyl ether, thereby generating precipitation of the desired acid addition salt.

The compounds of the invention inhibit the action of the thromboxane synthetase enzyme, but do not significantly inhibit the action of the prostacyclin synthetase or cyclo-oxygenase enzymes. Thus, the compounds are useful in treating conditions characterized by an imbalance of prostacyclin/thromboxane $A_2$, including such conditions as migraine headache, ischaemic heart disease, stroke and transient ischaemic attack, as hereinafter explained below.

For instance, research work has definitely established that in most tissues the major product of the arachidonic acid metabolism is either of two unstable substances, viz., thromboxane $A_2$ ($TxA_2$) or prostacyclin ($PGI_2$) (Proc. Nat. Acad. Sci. U.S.A., 1975, 72, 2994; Nature, 1976, 263, 663; Prostaglandins, 1976, 12, 897). In most cases, the prostaglandins $PGE_2$, $PGE_{2\alpha}$ and $PGD_2$ are comparatively minor by-products in this particular biosynthetic pathway. The discovery of thromboxane $A_2$ and prostacyclin has significantly increased our understanding of vascular homeostasis. Prostacyclin, for example, is a powerful vasodilator and an inhibitor of platelet aggregation and in this last respect, it is the most potent endogenous substance so far discovered. The prostacyclin synthetase enzyme is located in the endothelial layer of the vasculature and is fed by endoperoxides released by blood platelets coming into contact with the vessel wall. The prostacyclin thus produced is important for prevention of platelet deposition on vessel walls (Prostaglandins, 1976, 12, 685; Science, 1976, 17; Nature, 1978, 273, 765).

Thromboxane $A_2$, on the other hand, is synthesized by the thromboxane synthetase enzyme which is located in, for example, the blood platelets. Thromboxane $A_2$ is a powerful vasoconstrictor and pro-aggregatory substance. As such, its actions are in direct opposition to those of prostacyclin. If, for any reason, prostacyclin formation by the vasculature is impaired, then the endoperoxides produced by platelets coming into contact with the vessel wall are converted into thromboxane, but are not converted effectively into prostacyclin (Lancet, 1977, (i), 18; Prostaglandins, 1978, 13, 3). Alteration of the prostacyclin/thromboxane balance in favor of the latter substance could result in platelet aggregation, vasospasm (Lancet, 1977, (i), 479; Science, 1976, 1135; Amer. J. Cardiology, 1978, 41, 787) and an increased susceptibility to atherothrombosis (Lancet, 1977, (i), 1216). It is also known that in experimental atherosclerosis, prostacyclin generation is suppressed and thromboxane $A_2$ production is enhanced (Prostaglandins, 1977, 14, 1025 and 1035).

Thus, thromboxane $A_2$ has been implicated as the causative agent in variant angina, myocardial infarction, sudden cardiac death and stroke (Thromb. Haemostasis, 1977, 38, 132). Studies in rabbits have shown that electro-cardiagram (ECG) changes typical of these conditions were produced when freshly prepared thromboxane $A_2$ was injected directly into the animal's heart (N. Kharasch and J. Fried, Editors, "Biochemical Aspects of Prostaglandins and Thromboxanes", Academic Press, Inc., New York, 1977, p. 189). This technique is considered to represent a unique animal model of the heart attacks of coronary patients and has been used to show that administration of a compound believed to antagonize the effects of thromboxane $A_2$ protects the rabbits from the adverse consequences of thromboxane $A_2$ injection.

Another area where a $PGI_2/TxA_2$ imbalance is considered to be a contributory factor is that of migraine. The migraine headache is associated with changes in intra- and extra-cerebral blood flow and in particular, it involved a pre-headache reduction of cerebral blood flow, followed by dilation in both vascular areas during the headache phase. Prior to the development of the headache, blood levels of 5-hydroxytryptamine are elevated and this suggests the occurrence of in vivo aggregation and release of the amine from the platelet stores. It is known that the blood platelets of migraine patients are more prone to aggregate than are those of normal individuals (J. Clin. Pathol., 1971, 24, 250; J. Headache, 1977, 17, 101). Furthermore, it has now been postulated that not only is an abnormality of platelet function a major factor in the pathogenesis of migraine attacks, but it is also, in fact, their prime cause (Lancet, (i), 1978, 501). Thus, a drug that selectively modifies platelet function to inhibit thromboxane $A_2$ formation would have to be of considerable benefit in migraine therapy.

Aspirin and most other non-steroidal anti-inflammatory (NSAI) drugs inhibit the cyclo-oxygenase enzyme. The effect of this action is to shut down the production of the $PGG_2/H_2$ endoperoxides and by so doing, to reduce both the prostacyclin and thromboxane $A_2$ levels. Aspirin and aspirin-like drugs have been evaluated clinically for the prevention of stroke and heart attack (New England J. Med., 1978, 299, 53; Brit. Med. J., 1978, 1188; Stroke, 1977, 8, 301). Although some encouraging results have been obtained with these drugs, a compound which specifically inhibits thromboxane $A_2$ formation while simultaneously leaving the biosynthesis of prostacyclin unimpaired would, of course, necessarily be more valuable in these same clinical conditions (Lancet, (ii), 1978, 780).

The effect of the compounds of the formula (I) on the thromboxane synthetase enzyme, and the prostacyclin synthetase and cyclo-oxygenase enzymes has been measured by the following in vitro enzyme assay tests:

1. Cyclo-oxygenase

Ram seminal vesicle microsomes (Biochemistry, 1971, 10, 2372) are incubated with arachidonic acid (100 μM) at 22° C. for a period of one minute so as to produce $PGH_2$, and aliquots of this reaction mixture are then injected into a stream of Krebs-bicarbonate at 37° C. [containing a mixture of antagonists (Nature, 1978, 218, 1135) and indomethacin (Brit. J. Pharmacol., 1972, 45, 451)] which is superfusing a spirally-cut rabbit aorta strip (Nature, 1969, 223, 29). The ability of a compound to inhibit the enzyme is measured by comparing the increases in isometric tension produced by $PGH_2$ in the absence of the test compound and again, following pre-incubation of the enzyme with the test compound for a period of five minutes.

2. Prostacyclin ($PGI_2$) Synthetase

Pig aorta microsomes (Nature, 1976, 263, 663) are incubated with $PGH_2$ (produced as in enzyme assay test No. 1) at 22° C. for a period of 30 seconds and aliquots are then bio-assayed in the same manner as hereinbefore described. $PGI_2$ production is assessed indirectly by measuring the decrease in $PGH_2$-induced tension ($PGI_2$ itself does not contract the aorta). This decrease in tension can be prevented completely by pre-incubation of the enzyme with the selective $PGI_2$ synthetase inhibitor, known chemically as 15-hydroperoxy-arachidonic acid (Prostaglandins, 1976, 12, 715). The test compound is then pre-incubated with the enzyme for a period of five minutes and its ability to prevent the decrease in tension is subsequently measured.

3. Thromboxane $A_2$ ($TxA_2$) Synthetase

Indomethacin-pretreated human platelet microsomes (Science, 1976, 193, 163) are incubated with $PGH_2$ (produced as described in test No. 1) at 0° C. for a period of two minutes, and aliquots of the reaction mixture are then superfused over two rabbit aorta spirals which are separated by a delay coil (2 min.). The latter is required in order to allow for the selective decay of the more unstable thromboxane $A_2$ (Proc. Nat. Acad. Sci., 1975, 72, 2994), thereby enabling separate measurement of the increased isometric tension due to the $TxA_2$ formed and the $PGH_2$ remaining to take place. The test compound is then pre-incubated with the enzyme for a period of five minutes, and its ability to inhibit the thromboxane synthetase enzyme is measured as its reduction of the $TxA_2$ component of the isometric tension.

Compounds of the invention, when tested in this way, have been shown to be capable of selectively inhibiting the thromboxane synthetase enzyme.

In addition to the above, an in vitro assay test for measuring the inhibition of human blood platelet aggregation has been described and this may be considered predictive of anti-thrombotic efficacy from a clinical point of view (e.g., see Lancet, (ii), 1974, 1223 and J. Exp. Med., 1967, 126, 171). For example, both the clinically-effective agents known as aspirin and sulphinpyrazone, respectively, show inhibitory activity in vitro against a variety of aggregating agents employed in this test.

A number of in vivo tests in animals have also been described for evaluating potential anti-thrombotic drugs. For instance, intravenous injection of arachidonic acid causes death in rabbits by causing platelet clumping and embolization in the lungs. Again, both the clinically-effective aspirin (Agents and Actions, 1977, 1, 481) and sulphinpyrazone (Pharmacology, 1976, 14, 522) protect the rabbit from the lethal effect of the injection. Sulphinpyrazone has also been shown to prevent the aggregation of platelets in an extra corporeal loop of the abdominal aorta of rats in vivo (Thromb. Diathes. Haemostasis, 1973, 30, 138).

Again, the compounds of the present invention are considered to be effective inhibitors of human blood platelet aggregation when subjected to the above in vitro assay, in addition to being useful in protecting rabbits against the lethal effect of arachidonic acid injection and in preventing the aggregation of blood platelets in the rat aorta.

The compounds can be administered orally in the form of tablets or capsules containing a unit dose of the compound together with such excipients as corn starch, calcium carbonate, dicalcium phosphate, alginic acid, lactose, magnesium stearate and talc. The tablets are typically prepared by granulating the ingredients together and compressing the resulting mixture into tablets of the desired size. The capsules are typically prepared by granulating the ingredients together and filling them into hard gelatin capsules of the appropriate size to contain the proper ingredients.

The compounds can also be administered parenterally, for example, by intramuscular, intravenous or subcutaneous injection, or even by infusion of a parenteral solution of same into a vein. For parenteral administration, in general, they are best used in the form of a sterile aqueous solution which may contain other solutes such as tonic and pH adjusters. The compounds may, e.g., be added to distilled water and the pH subsequently adjusted to a value in the range of pH 3–6 with the aid of an acid such as citric acid, lactic acid or hydrochloric acid, etc. A sufficient amount of other solutes such as dextrose or saline may then be added to the mixture to render the final solution isotonic. The resulting solution is then sterilized according to the method of British Pharmacopoeia, 1973 by filtration through a bacteria-proof filter under aseptic conditions into sterile containers, so as to comply with the test for sterility of Appendix 121 in British Pharmacopoeia, 1973. Suitable containers for these purposes include, for example, sterile glass vials of an appropriate size to contain the desired volume of solution, which volume will typically contain a unit dose of the compound of the formula (I).

For oral administration to human patients, it is expected that the daily dosage level of a compound to be administered will be from about 0.1 to 20 mg./kg. per day for a typical adult patient (70 kg.). For parenteral administration, it is expected that the daily dosage level of a compound of the formula (I) will be from about 0.01–0.5 mg./kg. per day, for a typical adult patient. Thus, tablets or capsules can generally be expected to contain anywhere from approximately 5 to 150 mg. of the active compound for administration orally up to three times a day, while dosage units for parenteral administration can be expected to contain roughly from 0.5–35 mg. of the active compound on this basis. A typical vial used in the latter connection would be a 10 ml. vial containing 5 mg. of the active compound made up in 6–10 ml. of sterile solution.

It will, of course, be appreciated that the physician will, in any event, determine the actual dosage to be employed for the present purposes at hand and that this will be the dosage which is most suitable for the individual and it will vary with the age, weight and response of the patient. The above dosages are merely exemplary of the average host. There may, of course, be individual cases where higher or lower dosages are clearly called for, i.e., dosages which are above or below the limits set forth by the aforementioned ranges.

Preparation A

To a well-stirred solution of 2-isopropylindole (9.9 g.) in ethanol (30 ml.) at 0° C., there was added a 33% (w./w.) solution of dimethylamine in ethanol (10 ml.) and glacial acetic acid (3.5 ml.). A solution of 40% (w./v.) aqueous formaldehyde (5 ml.) was then added dropwise to the mixture, and the resulting solution was stirred at 5° C. for a period of one hour. Ice/water was next added to the reaction mixture, followed by excess solid potassium carbonate to give an orange oil. The liquid was then repeatedly extracted with diethyl ether (three times), using 50 ml. portions for each extraction. The combined ethereal extracts were then dried over anhydrous sodium sulfate and evaporated to give crude 3-(dimethylaminomethyl)-2-isopropylindole (4.5 g.) as a brown oil. The latter substance was used directly in Example I (as a starting material) without any further purification being necessary.

Preparation B

The other 3-(dimethylaminomethyl)indoles used as starting materials in Examples II–VI and VIII–XXV, respectively, are either known compounds or else they are easily prepared from the appropriately substituted indoles by methods similar to that described above in Preparation A.

Preparation C

The starting material used in Example VII, viz., 3-(α-dimethylaminoethyl)indole, is known from the prior art (Tetrahedron, 1973, 29, 3357) and is prepared according to the procedure described therein.

EXAMPLE I 3-(Dimethylaminomethyl)-2-isopropylindole (1.7 g.) and imidazole (0.6 g.) were heated at the reflux temperature in xylene (50 ml.) for a period of one hour. The solution was then cooled to room temperature (~20° C.) and petroleum ether (b.p. 60°–80° C.) was added until a faint cloudiness appeared. The resulting mixture was then allowed to stand at room temperature (~20° C.), whereupon the desired product soon crystallized from solution and was subsequently recovered by means of suction filtration. Recrystallization of the latter material from industrial methylated spirits (i.e., ethyl alcohol denatured with methanol) then gave pure 3-(imidazol-1-ylmethyl)-2-isopropylindole (yield, 0.5 g.), m.p. 241°–216° C.

Anal. Calcd. for $C_{15}H_{17}N_3$: C, 75.3; H, 7.15; N, 17.55. Found: C, 75.3; H, 7.2; N, 17.8.

EXAMPLE II

The procedure described in Example I was repeated except that 3-(dimethylaminomethyl)-2-methylindole was the starting material employed in place of 3-(dimethylaminomethyl)-2-isopropylindole, using the same molar proportions as before. In this particular case, the corresponding final product obtained was 3-(imidazol-1-ylmethyl)-2-methylindole, m.p. 145°–146° C. after recrystallization from ethyl acetate.

Anal. Calcd. for $C_{13}H_{13}N_3$: C, 73.9; H, 6.2; N, 19.9. Found: C, 74.05; H, 6.15; N, 20.1.

EXAMPLE III

The procedure described in Example I was repeated except that 3-(dimethylaminomethyl)-2-phenylindole was the starting material employed in place of 3-(dimethylaminomethyl)-2-isopropylindole, using the same molar proportions as before. In this particular case, the corresponding final product obtained was 3-(imidazol-1-ylmethyl)-2-phenylindole, m.p. 184°–185° C. after recrystallization from aqueous ethanol.

Anal. Calcd. for $C_{18}H_{15}N_3$: C, 79.1; H, 5.5; N, 15.4. Found: C, 79.0; H, 5.6; N, 15.4.

EXAMPLE IV

The procedure described in Example I was repeated except that 3-(dimethylaminomethyl)-5-methoxyindole was the starting material employed in place of 3-(dimethylaminomethyl)-2-isopropylindole, using the same molar proportions as before. In this particular case, the corresponding final product obtained was 3-(imidazol-1-ylmethyl)-5-methoxyindole, m.p. 156°–158° C. after recrystallization from ethyl acetate/petroleum ether (b.p. 60°–80° C.).

Anal. Calcd. for $C_{13}H_{13}N_3O$: C, 68.7; H, 5.8; N, 18.5. Found: C, 68.6; H, 5.8; N, 18.65.

EXAMPLE V

The procedure described in Example I was repeated except that 3-(dimethylaminomethyl)-5-methoxy-2-methylindole was the starting material employed in place of 3-(dimethylaminomethyl)-2-isopropylindole, using the same molar proportions as before. In this particular case, the corresponding final product obtained was 3-(imidazol-1-ylmethyl)-5-methoxy-2-methylindole, m.p. 147°–149° C. after recrystallization from ethyl acetate/petroleum ether (b.p. 60°–80° C.).

Anal. Calcd. for $C_{14}H_{15}N_3O$: C, 69.7; H, 6.3; N, 17.4. Found: C, 69.3; H, 6.4; N, 17.6.

EXAMPLE VI

The procedure described in Example I was repeated except that 3-(dimethylaminomethyl)-2-tert-butylindole was the starting material employed in place of 3-(dimethylaminomethyl)-2-isopropylindole, using the same molar proportions as before. In this particular case, the corresponding final product obtained was 3-(imidazol-1-ylmethyl)-2-tert-butylindole, m.p. 215°–216° C. after recrystallization from aqueous ethanol.

Anal. Calcd. for $C_{16}H_{19}N_3$: C, 75.85; H, 7.55; N, 16.6. Found: C, 76.0; H, 7.5; N, 16.8.

EXAMPLE VII

The procedure described in Example I was repeated except that 3-(α-dimethylaminoethyl)indole was the starting material employed in place of 3-(dimethylaminomethyl)-2-isopropylindole, using the same molar proportions as before. In this particular case, the corresponding final product obtained was 3-[α-(imidazol-1-yl)ethyl]indole, m.p. 172°–173° C. after recrystallization from aqueous ethanol.

Anal. Calcd. for $C_{13}H_{13}N_3$: C, 73.9; H, 6.2; N, 19.9. Found: C, 73.6; H, 6.3; N, 19.6.

EXAMPLE VIII

The procedure described in Example I was repeated except that 5-fluoro-3-(dimethylaminomethyl)indole was the starting material employed in place of 3-(dimethylaminomethyl)-2-isopropylindole, using the same molar proportions as before. In this particular case, the corresponding final product obtained was 5-fluoro-3-(imidazol-1-ylmethyl)indole, m.p. 168°–170° C. after recrystallization from ethyl acetate.

Anal. Calcd. for $C_{12}H_{10}FN_3$: C, 66.96; H, 4.68; N, 19.53. Found: C, 66.89; H, 4.63; N, 19.71.

EXAMPLE IX

The procedure described in Example I was repeated except that 5-bromo-3-(dimethylaminomethyl)indole was the starting material employed in place of 3-(dimethylaminomethyl)-2-isopropylindole, using the same molar proportions as before. In this particular case, the corresponding final product obtained was 5-bromo-3-(imidazol-1-ylmethyl)indole, m.p. 198°–201° C. after recrystallization from methyl ethyl ketone.

Anal. Calcd. for $C_{12}H_{10}BrN_3$: C, 52.19; H, 3.65; N, 15.22. Found: C, 52.34; H, 3.56; N, 15.57.

EXAMPLE X

The procedure described in Example I was repeated except that 3-(dimethylaminomethyl)-7-methylindole was the starting material employed in place of 3-(dimethylaminomethyl)-2-isopropylindole, using the same molar proportions as before. In this particular case, the corresponding final product obtained was 3-(imidazol-1-ylmethyl)-7-methylindole, m.p. 201°–203° C. after recrystallization from methyl ethyl ketone/petroleum ether (b.p. 60°–80° C.).

Anal. Calcd. for $C_{13}H_{13}N_3$: C, 73.90; H, 6.20; N, 19.89. Found: C, 73.68; H, 6.25; N, 19.83.

EXAMPLE XI

The procedure described in Example I was repeated except that 3-(dimethylaminomethyl)-5-methylindole was the starting material employed in place of 3-(dimethylaminomethyl)-2-isopropylindole, using the same molar proportions as before. In this particular case, the corresponding final product obtained was 3-(imidazol-1-ylmethyl)-5-methylindole, m.p. 189°–191° C. after recrystallization from methyl ethyl ketone/petroleum ether (b.p. 60°–80° C.).

Anal. Calcd. for $C_{13}H_{13}N_3$: C, 73.90; H, 6.20; N, 19.89. Found: C, 73.55; H, 6.21; N, 19.94.

EXAMPLE XII

The procedure described in Example I was repeated except that 2-cyclohexyl-3-(dimethylaminomethyl)indole was the starting material employed in place of 3-(dimethylaminomethyl)-2-isopropylindole, using the same molar proportions as before. In this particular case, the corresponding final product obtained was 2-cyclohexyl-3-(imidazol-1-ylmethyl)indole, m.p. 224°–226° C. after recrystallization from industrial methylated spirits.

Anal. Calcd. for $C_{18}H_{21}N_3$: C, 77.38; H, 7.58; N, 15.04. Found: C, 77.10; H, 7.59; N, 15.05.

EXAMPLE XIII

The procedure described in Example I was repeated except that 2-cyclopropyl-3-(dimethylaminomethyl)indole was the starting material employed in place of 3-(dimethylaminomethyl)-2-isopropylindole, using the same molar proportions as before. In this particular case, the corresponding final product obtained was 2-cyclopropyl-3-(imidazol-1-ylmethyl)indole, m.p. 174°–176° C. after recrystallization from toluene.

Anal. Calcd. for $C_{15}H_{15}N_3$: C, 75.92; H, 6.37; N, 17.71. Found: C, 76.42; H, 6.48; N, 17.52.

EXAMPLE XIV

The procedure described in Example I was repeated except that 2-adamantyl-3-(dimethylaminomethyl)indole was the starting material employed in place of 3-(dimethylaminomethyl)-2-isopropylindole, using the same molar proportions as before. In this particular case, the corresponding final product obtained was 2-adamantyl-3-(imidazol-1-ylmethyl)indole, m.p. 266°–268° C. after recrystallization from ethyl acetate containing a trace of methanol.

Anal. Calcd. for $C_{22}H_{25}N_3$: C, 79.72; H, 7.60; N, 12.68. Found: C, 79.04; H, 7.75; N, 11.96.

EXAMPLE XV

The procedure described in Example I was repeated except that 3-(dimethylaminoethyl)-2-(o-tolyl)indole was the starting material employed in place of 3-(dimethylaminomethyl)-2-isopropylindole, using the same molar proportions as before. On this particular case, the corresponding final product obtained was 3-(imidazol-1-ylmethyl)-2-(o-tolyl)indole, m.p. 156°–158° C. after recrystallization from ethyl acetate/petroleum ether (b.p. 80°–100° C.).

Anal. Calcd. for $C_{19}H_{17}N_3$: C, 79.41; H, 5.96; N, 14.62. Found: C, 79.22; H, 6.19; N, 14.53.

EXAMPLE XVI

The procedure described in Example I was repeated except that 3-(dimethylaminomethyl)-5-methoxy-2-(o-tolyl)indole was the starting material employed in place of 3-(dimethylaminomethyl)-2-isopropylindole, using the same molar proportions as before. In this particular case, the corresponding final product obtained was 3-(imidazol-1-ylmethyl)-5-methoxy-2-(o-tolyl)indole, m.p. 145°–147° C. after recrystallization from isopropanol/petroleum ether (b.p. 60°–80° C.).

Anal. Calcd. for $C_{20}H_{19}N_3O$: C, 75.68; H, 6.03; N, 13.24. Found: C, 76.01; H, 6.09; N, 13.33.

EXAMPLE XVII

The procedure described in Example I was repeated except that 3-(dimethylaminomethyl)-2-(p-tolyl)indole was the starting material employed in place of 3-(dimethylaminomethyl)-2-isopropylindole, using the same molar proportions as before. In this particular case, the corresponding final product obtained was 3-(imidazol-1-ylmethyl)-2-(p-tolyl)indole, m.p. 194°–196° C. after recrystallization from ethyl acetate.

Anal. Calcd. for $C_{19}H_{17}N_3$: C, 79.41; H, 5.96; N, 14.62. Found: C, 78.92; H, 6.01; N, 14.46.

EXAMPLE XVIII

The procedure described in Example I was repeated except that 2-(o-anisyl)-3-(dimethylaminomethyl)indole was the starting material employed in place of 3-(dimethylaminomethyl)indole, using the same molar proportions as before. In this particular case, the corresponding final product obtained was 2-(o-anisyl)-3-(imidazol-1-ylmethyl)indole, m.p. 199°–201° C. after recrystallization from methanol.

Anal. Calcd. for $C_{19}H_{17}N_3O$: C, 75.22; H, 5.65; N, 13.85. Found: C, 75.44; H, 5.77; N, 13.80.

EXAMPLE XIX

The procedure described in Example I was repeated except that 2-(p-anisyl)-3-(dimethylaminomethyl)indole was the starting material employed in place of 3-(dimethylaminomethyl)-2-isopropylindole, using the same molar proportions as before. In this particular case, the corresponding final product obtained was 2-(p-anisyl)-3-(imidazol-1-ylmethyl)indole, m.p. 198°–199° C. after recrystallization from ethyl acetate.

Anal. Calcd. for $C_{19}H_{17}N_3O$: C, 75.22; H, 5.65; N, 13.85. Found: C, 74.71; H, 5.62; N, 13.52.

EXAMPLE XX

The procedure described in Example I was repeated except that 2-(o-chlorophenyl)-3-(dimethylaminomethyl)indole was the starting material employed in place of 3-(dimethylaminomethyl)-2-isopropylindole, using the same molar proportions as before. In this particular case, the corresponding final product obtained was 2-(o-chlorophenyl)-3-(imidazol-1-ylmethyl)indole, m.p. 235°–237° C. after recrystallization from methanol.

Anal. Calcd. for $C_{18}H_{14}ClN_3$: C, 70.24; H, 4.58; N, 13.65. Found: C, 70.13; H, 4.59; N, 13.60.

EXAMPLE XXI

The procedure described in Example I was repeated except that 2-(p-chlorophenyl)-3-(dimethylaminomethyl)indole was the starting material employed in place of 3-(dimethylaminomethyl)-2-isopropylindole, using the same molar proportions as before. In this particular case, the corresponding final product obtained was 2-(p-chlorophenyl)-3-imidazol-1-ylmethyl)indole, m.p. 208°–209° C. after recrystallization from methanol.

Anal. Calcd. for $C_{18}H_{14}ClN_3$: C, 70.24; H, 4.58; N, 13.65. Found: C, 69.79; H, 4.66; N, 13.78.

EXAMPLE XXII

The procedure described in Example I was repeated except that 2-benzyl-3-(dimethylaminomethyl)indole was the starting material employed in place of 3-(dimethylaminomethyl)-2-isopropylindole, using the same molar proportions as before. In this particular case, the corresponding final product obtained was 2-benzyl-3-(imidazol-1-ylmethyl)indole, m.p. 159°–160° C. after recrystallization from ethanol/water.

Anal. Calcd. for $C_{19}H_{17}N_3$: C, 79.41; H, 5.96; N, 14.62. Found: C, 79.24; H, 6.01; N, 14.89.

EXAMPLE XXIII

The procedure described in Example I was repeated except that 5-dimethylamino-3-(dimethylaminomethyl)indole was the starting material employed in place of 3-(dimethylaminomethyl)-2-isopropylindole, using the same molar proportions as before. In this particular case, the corresponding final product obtained was 5-dimethylamino-3-(imidazol-1-ylmethyl)indole, m.p. 151°–152° C. after recrystallization from ethyl acetate containing a trace of methanol.

Anal. Calcd. for $C_{14}H_{16}N_4$: C, 69.97; H, 6.71; N, 23.32. Found: C, 69.79; H, 6.78; N, 23.01.

EXAMPLE XXIV

The procedure described in Example I was repeated except that 3-(dimethylaminomethyl)-6-trifluoromethylindole was the starting material employed in place of 3-(dimethylaminomethyl)-2-isopropylindole, using the same molar proportions as before. In this particular case, the corresponding final product obtained was 3-(imidazol-1-ylmethyl)-6-trifluoromethylindole, m.p. 171° C. after recrystallization from ethyl acetate/petroleum ether (b.p. 40°–60° C.).

Anal. Calcd. for $C_{13}H_{10}F_3N_3$: C, 58.87; H, 3.80; N, 15.84. Found: C, 58.87; H, 3.80; N, 15.83.

EXAMPLE XXV

The procedure described in Example I was repeated except that 5-benzyloxy-3-(dimethylaminomethyl)indole was the starting material employed in place of 3-(dimethylaminomethyl)-2-isopropylindole, using the same molar proportions as before. In this particular case, the corresponding final product obtained was 5-benzyloxy-3-(imidazol-1-ylmethyl)indole, m.p. 194°–196° C. after recrystallization from 2-butanone/petroleum ether (b.p. 60°–80° C.).

Anal. Calcd. for $C_{19}H_{17}N_3O$: C, 75.22; H, 5.65; N, 13.85. Found: C, 75.07; H, 5.69; N, 13.54.

EXAMPLE XXVI 3-(Imidazol-1-ylmethyl)indole, (1.97 g., 0.01 mole) was dissolved in dry dimethylformamide (10 ml) and sodium hydride (0.32 g., 80% dispersion in mineral oil) was added thereto in small portions with cooling. The resulting solution was stirred at room temperature (~20° C.) for a period of 30 minutes, followed by the addition of benzyl bromide (1.71 g., 0.01 mole) in a dropwise manner during the course of a period of two minutes with cooling. The spent reaction mixture was then stirred at room temperature (20° C.) for a period of two hours and finally poured into water to give an oil which soon solidified. The solidified oil/water mixture was then extracted with ethyl acetate, and the resulting organic phase was washed well with water and subsequently dried over anhydrous sodium sulfate. Evaporation of the organic phase then gave an oil which again solidified on standing. The solid material was dissolved in a small volume of ethanol and an excess of ethereal hydrogen chloride was added to the mixture, resulting in the precipitation of the hydrochloride salt of the desired product in the form of an oil, which thereafter soon solidified on standing. The latter material was then recrystallized twice from methyl ethyl ketone/diethyl ether to yield 1.1 g. (34%) of pure 1-benzyl-3-(imidazol-1-ylmethyl)indole hydrochloride, m.p. ;b 126°–129° C.

Anal. Calcd. for $C_{19}H_{17}N_3.HCl$: C, 70.47; H, 5.60; N, 12.98. Found: C, 70.14; H, 5.53; N, 12.72.

EXAMPLE XXVII

The procedure described in Example XXVI was repeated except that dimethyl sulfide was the alkylating agent of choice employed instead of benzyl bromide (on the same molar basis as before). The crude product so obtained was then purified by means of column chromatography over silica gel. Elution with petroleum ether (b.p. 60°–80° C.) then removed the mineral oil and the pure product was finally eluted with chloroform. In this manner, there was ultimately obtained pure 3-(imidazol-1-ylmethyl)-1-methylindole as the free base compound, m.p. 86°–89° C. after recrystallization from benzene/petroleum ether (b.p. 60°–80° C.).

Anal. Calcd. for $C_{13}H_{13}N_3$: C, 73.90; H, 6.20; N, 19.89. Found: C, 73.61; H, 6.24; N, 19.79.

EXAMPLE XXVIII

The procedure described in Example XXVI was repeated except that 3-[α-(imidazol-1-yl)ethyl]indole was the starting material employed in place of 3-(imidazol-1-ylmethyl)indole, while methyl iodide was the alkylating agent of choice used instead of benzyl bromide (on the same molar basis as before). The crude product so attained was then purified by means of column chromatography over silica gel. Elution with petroleum ether (b.p. 60°–80° C.) then removed the mineral oil and the pure product was finally eluted with chloroform. In this manner, there was ultimately obtained pure 3-[α-(imidazol-1-yl)ethyl]-1-methylindole, isolated as the fumarate salt, m.p. 116°–118° C. after recrystallization from ethyl acetate.

Anal. Calcd. for $C_{14}H_{15}N_3 \cdot C_4H_4O_4$: C, 63.33; H, 5.61; N, 12.31. Found: C, 62.67; H, 5.59; N, 12.01.

EXAMPLE XXIX

The procedure described in Example XXVI was repeated except that diethyl sulfate was the alkylating agent of choice employed instead of benzyl bromide (on the same molar basis as before). The crude product so obtained was then purified by means of column chromatography over silica gel. Elution with petroleum ether (b.p. 60°–80° C.) then removed the mineral oil and the pure product was finally eluted with chloroform. In this manner, there was ultimately obtained pure 1-ethyl-3-(imidazol-1-ylmethyl)indole, isolated as the maleate salt, m.p. 106°–107° C. after recrystallization from ethyl acetate containing a trace of methanol.

Anal. Calcd. for $C_{14}H_{15}N_3 \cdot C_4H_4O_4$: C, 63.33; H, 5.61; N, 12.31. Found: C, 63.28; H, 5.67; N, 12.04.

EXAMPLE XXX

The procedure described in Example XXVI was repeated except that n-propyl iodide was the alkylating agent of choice employed instead of benzyl bromide (on the same molar basis as before). The crude product so obtained was then purified by means of column chromatography over silica gel. Elution with petroleum ether (b.p. 60°–80° C.) then removed the mineral oil and the pure product was finally eluted with chloroform. In this manner, there was ultimately obtained pure 3-(imidazol-1-ylmethyl)-1-(n-propyl)indole, isolated as the fumarate salt, m.p. 126°–127° C. after recrystallization from ethyl acetate containing a trace of methanol.

Anal. Calcd. for $C_{15}H_{17}N_3 \cdot C_4H_4O_4$: C, 64.21; H, 5.96; N, 11.83. Found: C, 63.92; H, 5.96; N, 11.84.

EXAMPLE XXXI

The procedure described in Example XXVI was repeated except that allyl bromide was the alkylating agent of choice employed instead of benzyl bromide (on the same molar basis as before). The crude product so obtained was then purified by means of column chromatography over silica gel. Elution with petroleum ether (b.p. 60°–80° C.) then removed the mineral oil and the pure product was finally eluted with chloroform. In this manner, there was ultimately obtained pure 1-allyl-3-(imidazol-1-ylmethyl)indole, isolated as the fumarate salt, m.p. 120°–121° C. after recrystallization from ethyl acetate containing a trace of methanol.

Anal. Calcd. for $C_{15}H_{15}N_3 \cdot C_4H_4O_4$: C, 64.58; H, 5.42; N, 11.89. Found: C, 64.72; H, 5.09; N, 12.11.

EXAMPLE XXXII

The procedure described in Example XXVI was repeated except that 3-[α-(imidazol-1-yl)ethyl]indole was the starting material employed in place of 3-(imidazol-1-ylmethyl)indole, while allyl bromide was the alkylating agent of choice used instead of benzyl bromide (on the same molar basis as before). The crude product so obtained was then purified by means of column chromatography over silica gel. Elution with petroleum ether (b.p. 60°–80° C.) then removed the mineral oil and the pure product was finally eluted with chloroform. In this manner, there was ultimately obtained pure 1-allyl-3-[α-(imidazol-1-yl)ethyl]indole, isolated as the fumarate salt, m.p. 113°–114° C. after recrystallization from ethyl acetate.

Anal. Calcd for $C_{16}H_{17}N_3 \cdot C_4H_4O_4$: C, 65.38; H, 5.76; N, 11.44. Found: C, 65.34; H, 5.67; N, 11.55.

EXAMPLE XXXIII

The procedure described is Example XXVI was repeated except that 3-(imidazol-1-ylmethyl)-5-methoxyindole was the starting material employed in place of 3-(imidazol-1-ylmethyl)-indole and allyl bromide was the alkylating agent of choice used instead of benzyl bromide (on the same molar basis as before). The crude product so obtained was then purified by means of column chromatography over silica gel. Elution with petroleum ether (b.p. 60°–80° C.) then removed the mineral oil and the pure product was finally eluted with chloroform. In this manner, there was ultimately obtained pure 1-allyl-3-(imidazol-1-ylmethyl)-5-methoxyindole, isolated as the oxalate salt, m.p. 129°–130° C. after recrystallization from ethanol/diethyl ether.

Anal. Calcd. for $C_{16}H_{17}N_3O \cdot C_2H_2O_4$: C, 60.5; H, 5.35; N, 11.75. Found: C, 60.2; H, 5.33; N, 11.81.

EXAMPLE XXXIV

The procedure described in Example XXVI was repeated except that 5-bromo-3-(imidazol-1-ylmethyl)indole was the starting material employed in place of 3-(imidazol-1-ylmethyl)indole and allyl bromide was the alkylating agent of choice used instead of benzyl bromide (on the same molar basis as before). The crude product so obtained was then purified by means of column chromatography over silica gel. Elution with petroleum ether (b.p. 60°–80° C.) then removed the mineral oil and the pure product was finally eluted with chloroform. In this manner, there was ultimately obtained pure 1-allyl-5-bromo-3-(imidazol-1-ylmethyl)indole, isolated as the oxalate salt after recrystallization from ethanol/diethyl ether; m.p. 175°–177° C.

Anal. Calcd. for $C_{15}H_{14}BrN_3 \cdot C_2H_2O_4$: C, 50.26; H, 3.97; N, 10.34. Found: C, 50.42; H, 3.91; N, 10.50.

EXAMPLE XXXV

The procedure described in Example XXVI was repeated except that methallyl bromide was the alkylating agent of choice employed instead of benzyl bromide (on the same molar basis as before). The crude product so obtained was then purified by means of column chromatography over silica gel. Elution with petroleum ether (b.p. 60°–80° C.) then removed the mineral oil and the pure product was finally eluted with chloroform. In this manner, there was ultimately obtained pure 3-(imidazol-1-yl-methyl)-1-methallylindole, isolated as the fumarate salt, m.p. 141°–142° C. after recrystallization from ethyl acetate containing a trace of methanol.

Anal. Calcd. for $C_{16}H_{17}N_3 \cdot C_4H_4O_4$: C, 65.38; H, 5.76; N, 11.44. Found: C, 65.69; H, 5.88; N, 11.54.

EXAMPLE XXXVI

The procedure described in Example XXVI was repeated except that cyclopropylmethyl bromide was the alkylating agent of choice employed instead of benzyl bromide (on the same molar basis as before). The crude product so obtained was then purified by means of column chromatography over silica gel. Elution with petroleum ether (b.p. 60°-80° C.) then removed the mineral oil and the pure product was finally eluted with chloroform. In this manner, there was ultimately obtained pure 1-cyclopropylmethyl-3-(imidazol-1-ylmethyl)indole, isolated as the fumarate salt, m.p. 149°-150° C. after recrystallization from ethyl acetate containing a trace of methanol.

Anal. Calcd. for $C_{16}H_{17}N_3$: C, 65.38; H, 5.76; N, 11.44. Found: C, 65.32; H, 5.71; N, 11.24.

EXAMPLE XXXVII

The procedure described in Example XXVI was repeated except that β-methoxyethyl bromide was the alkylating agent of choice employed instead of benzyl bromide (on the same molar basis as before). The crude product so obtained was then purified by means of column chromatography over silica gel. Elution with petroleum ether (b.p. 60°-80° C.) then removed the mineral oil and the pure product was finally eluted with chloroform. In this manner, there was ultimately obtained pure 3-(imidazol-1-ylmethyl)-1-(β-methoxyethyl)indole, isolated as the fumarate salt, m.p. 105°-107° C. after recrystallization from ethyl acetate.

Anal. Calcd. for $C_{15}H_{17}N_3O$: C, 61.44; H, 5.70; N, 11.32. Found: C, 61.17; H, 5.71; N, 11.09.

EXAMPLE XXXVIII

The procedure described in Example XXVI was repeated except that β-dimethylaminoethyl chloride was the alkylating agent of choice employed instead of benzyl bromide (on the same molar basis as before). The crude product so obtained was then purified by means of column chromatography over silica gel. Elution with petroleum ether (b.p. 60°-80° C.) then removed the mineral oil and the pure product was finally eluted with chloroform/methanol (9:1 by volume). In this manner, there was ultimately obtained pure 1-(β-dimethylaminoethyl)-3-(imidazol-1-ylmethyl)indole, isolated as the bis-oxalate salt, m.p. 154°-156° C. after recrystallization from ethyl acetate containing a trace of methanol.

Anal. Calcd. for $C_{16}H_{20}N_4 \cdot 2C_2H_2O_4$: C, 53.57; H, 5.39; N, 12.38. Found: C, 53.17; H, 5.41; N, 12.38.

EXAMPLE XXXIX

The procedure described in Example XXVI was repeated except that p-chlorobenzyl chloride was the alkylating agent of choice employed instead of benzyl bromide (on the same molar basis as before). The crude product so obtained was then purified by means of column chromatography over silica gel. Elution with petroleum ether (b.p. 60°-80° C.) then removed the mineral oil and the pure product was finally eluted with chloroform. In this manner, there was ultimately obtained pure 1-(p-chlorobenzyl)-3-(imidazol-1-ylmethyl)indole, isolated as the hemi-fumarate salt, m.p. 160° C. after recrystallization from ethyl acetate containg a trace of methanol.

Anal. Calcd. for $C_{19}H_{16}ClN_3 \cdot 0.5C_4H_4O_4$: C, 66.40; H, 4.78; N, 11.06. Found: C, 66.85; H, 4.86; N, 11.19.

EXAMPLE XL

The procedure described in Example XXVI was repeated except that benzoyl chloride was the reagent (i.e., acylating agent) employed instead of benzyl bromide (on the same molar basis as before). The crude product so obtained was then purified by means of column chromatography over silica gel. Elution with petroleum ether (b.p. 60°-80° C.) then removed the mineral oil and the pure product was finally eluted with chloroform. In this manner, there was ultimately obtained pure 1-benzoyl-3-(imidazol-1-ylmethyl)indole as the free base compound, m.p. 121°-123° C.

Anal. Calcd. for $C_{19}H_{15}N_3O$: C, 75.73; H, 5.02; N, 13.95. Found: C, 75.46; H, 5.07; N, 13.83.

EXAMPLE XLI

The procedure described in Example XXVI was repeated except that cyclopropylcarbonyl chloride was the reagent (i.e., acylating agent) employed instead of benzyl bromide (on the same molar basis as before). The crude product so obtained was then purified by means of column chromatography over silica gel. Elution with petroleum ether (b.p. 60°-80° C.) than removed the mineral oil and the pure product was finally eluted with chloroform. In this manner, there was ultimately obtained pure 1-cyclopropylcarbonyl-3-(imidazol-1-ylmethyl)indole as the free base compound, m.p. 131°-132° C. after recrystallization from ethyl acetate/petroleum ether (b.p. 40°-60° C.).

Anal. Calcd. for $C_{16}H_{15}N_3O$: C, 72.43; H, 5.70; N, 15.84. Found: C, 72.06; H, 5.82; N, 16.02.

EXAMPLE XLII

The procedure described in Example XXVI was repeated except that p-methylbenzoyl chloride was the reagent (i.e., acylating agent) employed instead of benzyl bromide (on the same molar basis as before). The crude product so obtained was then purified by means of column chromatography over silica gel. Elution with petroleum ether (b.p. 60°-80° C.) then removed the mineral oil and the pure product was finally eluted with chloroform. In this manner, there was ultimately obtained pure 3-(imidazol-1-ylmethyl)-1-(p-methylbenzoyl)indole as the free base compound, m.p. 156° C. after recrystallization from toluene.

Anal. Calcd. for $C_{20}H_{17}N_3O$: C, 76.17; H, 5.44; N, 13.32. Found: C, 76.12; H, 5.37; N, 13.25.

EXAMPLE XLIII

The procedure described in Example XXVI was repeated except that p-methoxylbenzoyl chloride was the reagent (i.e., acylating agent) employed instead of benzyl bromide (on the same molar basis as before). The crude product so obtained was then purified by means of column chromatography over silica gel. Elution with petroleum ether (b.p. 60°-80° C.) then removed the mineral oil and the pure product was finally eluted with chloroform. In this manner, there was ultimately obtained pure 3-(imidazol-1-ylmethyl)-1-(p-methoxybenzoyl)indole as the free base compound, m.p. 132° C. after recrystallization from toluene.

Anal. Calcd. for $C_{20}H_{17}N_3O_2$: C, 72.49; H, 5.17; N, 12.68. Found: C, 72.10; H, 5.21; N, 12.57.

EXAMPLE XLIV

The procedure described in Example XXVI was repeated except that p-chlorobenzoyl chloride was the reagent (i.e., acylating agent) employed instead of benzyl bromide (on the same molar basis as before). The crude product so obtained was then purified by means of column chromatography over silica gel. Elution with petroleum ether (b.p. 60°–80° C.) then removed the mineral oil and the pure product was finally eluted with chloroform. In this manner, there was ultimately obtained pure 1-(p-chlorobenzoyl)-3-(imidazol-1-ylmethly)indole as the fumarate salt, m.p. 174°–175° C. after recrystallization from isopropanol.

Anal. Calcd. for $C_{19}H_{14}ClN_3O \cdot C_4H_4O_4$: C, 61.13; H, 4.01; N, 9.30. Found: C, 61.38; H, 4.04; N, 9.70.

EXAMPLE XLV

The procedure described in Example XXVI was repeated except that m-trifluoromethylbenzoyl chloride was the reagent (i.e., acylating agent) employed instead of benzyl bromide (on the same molar basis as before). The crude product so obtained was then purified by means of column chromatography over silica gel. Elution with petroleum ether (b.p. 60°–80° C.) then removed the mineral oil and the pure product was finally eluted with chloroform. In this manner, there was ultimately obtained pure 3-(imidazol-1-ylmethyl)-1-(m-trifluoromethylbenzoyl)indole, isolated as the fumarate salt, m.p. 152° C. after recrystallization from ethyl acetate containing a trace of isopropanol.

Anal. Calcd. for $C_{20}H_{14}F_3N_3O \cdot C_4H_4O_4$: C, 59.38; H, 3.74; N, 8.66. Found: C, 59.28; H, 3.97; N, 8.36.

EXAMPLE XLVI

A mixture consisting of 3-(imidazol-1-ylmethyl)indole (0.97 g) and 1-acetylimidazole (1.10 g) was heated on a steam bath for a period of 3.5 hours to give an orange oil, which soon solidified on cooling. The resulting solid product was then chromatographed on silica gel. Elution with chloroform first gave some minor impurity, followed by the pure product. The product-containing fractions were then combined and subsequently evaporated to dryness while under reduced pressure to afford a solid residue, which was thereafter crystallized from ethyl acetate to yield pure 1-acetyl-3-(imidazol-1-ylmethyl)indole (yield, 0.50 g.), m.p. 122° C.

Anal. Calcd. for $C_{14}H_{13}N_3O$: C, 70.28; H, 5.48; N, 17.56. Found: C, 70.18; H, 5.43; N, 17.42.

EXAMPLE XLVII

To a well-stirred solution consisting of 3-(imidazol-1-ylmethyl)-5-methoxyindole (0.30 g.) dissolved in dry methylene chloride (30 ml.) at −70° C., there was added boron tribromide (0.38 ml.) in a dropwise manner. The resulting mixture was allowed to warm up and was then stirred at 20° C. for a period of five hours. Water (50 ml.) was then added to the spent reaction mixture, and the resulting aqueous layer was subsequently separated and washed with methylene chloride (using two-20 ml. portions). The washed aqueous layer was then made basic with solid sodium bicarbonate and evaporated to dryness. The residue obtained in this manner was next treated with boiling ethyl acetate (200 ml.), and the resulting organic solution was separated from the mixture by decantation and then evaporated to give a solid. Crystallization of the latter material from isopropanol/petroleum ether (b.p. 80°–100° C.) then gave pure 5-hydroxy-3-(imidazol-1-ylmethyl)-indole (yield, 0.10 g.), m.p. 169°–170° C.

Anal. Calcd. for $C_{12}H_{11}N_3O$: C, 67.59; H, 5.20; N, 19.71. Found: C, 67.59; H, 5.32; N, 19.45.

EXAMPLE XLVIII

The procedure described in Example XLVII was repeated except that 1-allyl-3-(imidazol-1-ylmethyl)-5-methoxyindole (1.34 g.) and boron tribromide (1.91 ml.) were the reactant and reagent respectively employed under these same conditions. After basification with sodium bicarbonate, the aqueous layer was extracted with three-100 ml. portions of ethyl acetate and the combined organic extracts were washed with water and subsequently dried over anhydrous magnesium sulfate. Evaporation of the solvent then gave a solid product, which later was crystallized from ethanol to afford pure 1-allyl-5-hydroxy-3-(imidazol-1-ylmethyl)indole (yield, 0.56 g.), m.p. 165°–167° C.

Anal. Calcd. for $C_{15}H_{15}N_3O$: C, 71.12; H, 5.97; N, 16.59. Found: C, 70.72; H, 6.00; N, 16.79.

EXAMPLE XLIX

The procedure described in Example XLVII was repeated except that 3-(imidazol-1-ylmethyl)-5-methoxy-2-(o-tolyl)indole was the starting material employed in place of 3-(imidazol-1-ylmethyl)-5-methoxyindole, using the same molar proportions as before. In this particular case, the corresponding final product obtained was 5-hydroxy-3-(imidazol-1-ylmethyl)-2-(o-tolyl)indole, m.p. 217°–218° C. after recrystallization from ethanol/petroleum ether (b.p. 60°–80° C.).

Anal. Calcd for $C_{19}H_{17}N_3O$: C, 75.22; H, 5.65; N, 13.85. Found: C, 75.96; H, 5.99; N, 13.55.

EXAMPLE L

The procedure described in Example XLVII was repeated except that 2-(p-anisyl)-3-(imidazol-1-ylmethyl)indole was the starting material employed in place of 3-(imidazol-1-ylmethyl)-5-methoxyindole, using the same molar proportions as before. In this particular case, the solid product obtained was chromatographed on silica gel and then finally eluted with chloroform/methanol (20:1 by volume). Evaporation of the product-containing eluate then gave a solid material which was crystallized from ethanol to afford pure 2-(p-hydroxyphenyl)-3-(imidazol-1-ylmethyl)indole, m.p. 245°–247° C.

Anal. Calcd. for $C_{18}H_{15}N_3O$: C, 74.72; H, 5.23; N, 14.52. Found: C, 74.55: H, 5.35; N, 14.26.

EXAMPLE LI 3-(Imidazol-1-ylmethyl)-2-isopropylindole (250 mg.) was dissolved in the minimum amount of ethanol (1.5 ml.) necessary to effect said solution with the aid of gentle warming. The latter alcoholic solution was then added dropwise to ethereal hydrogen chloride (15 ml.) to give a clear solution, which was thereafter allowed to stand for 10 minutes so as to permit precipitation of the desired hydrogen chloride acid addition salt to occur. The latter salt was recovered by means of suction filtration and recrystallized from ethyl acetate containing a trace of methanol to afford pure 3-(imidazol-1-ylmethyl)-2-isopropylindole hydrochloride. The yield of pure product (salt) melting at 187°–188° C. amounted to 230 mg. after first having been air dried to constant weight at 100° C. for a period of four hours.

Anal. Calcd. for $C_{15}H_{17}N_3 \cdot HCl$: C, 65.26; H, 6.52; N, 15.23. Found: C, 64.57; H, 6.58; N, 15.57.

EXAMPLE LII 3-(Imidazol-1-ylmethyl)indole (1.0 g.) was added to distilled water (900 ml.) and the resulting mixture adjusted to pH 5 with hydrochloric acid. Sodium chloride (18 g.) was then added and the solution was made up to two liters (with more distilled water). The final aqueous solution was then sterilized according to the procedure of the *British Pharmacoplia* (1973) by filtration through a suitable bacteria-proof filter under aseptic conditions into appropriate sterile containers, so as to comply with the test for sterility in Appendix 121 of the aforementioned reference text. Suitable sterile containers for use in this connection are 10 ml. glass vials (sterile), which are filled with 10 ml. of the final aqueous preparation so that the resulting filled vials each contain 5 mg. of the active ingredient.

EXAMPLE LIII

A dry solid pharmaceutical composition suitable for preparing capsules therefrom is prepared by combining the following materials together in the proportions by weight indicated below:

| | |
|---|---|
| 3-(Imidazol-1-ylmethyl)indole | 20 |
| Lactose | 250 |
| Maize stearch | 75 |
| Magnesium stearate | 5 |

The dried solid mixture so prepared is then thoroughly agitated so as to obtain a powdered product that is completely uniform in every respect. Hard-filled gelatin capsules containing this pharmaceutical composition are then prepared, employing a sufficient quantity of material in each instance so as to provide each capsule with 20 mg. of the active ingredient.

EXAMPLE LIV

Compounds of the invention have been tested by the in vitro enzyme assays hereinbefore described and the results of these tests are shown below in the following table, which gives the molar concentration of each compound which caused a 50% change in the effect of the relevant enzyme on isometric tension, i.e., caused a 50% inhibition of the actions of that enzyme. The table also shows a comparison (in tabular form) of the ratios of those molar concentrations causing a 50% inhibition in activity of the prostacyclin synthetase and thromboxane synthetase enzymes, respectively, thereby providing a clear indication of the ability of these particular compounds to selectively inhibit the action of the latter enzyme relative to the former.

| Example No. of Compound | Concentration causing 50% inhibition of | | | Ratio of (3) to (1) |
|---|---|---|---|---|
| | (1) thromboxane synthetase | (2) cyclo-oxygenase | (3) prostacyclin synthetase | |
| * | $3.0 \times 10^{-8}$ | $>10^{-3}$ | $6.5 \times 10^{-4}$ | 22,000 |
| I | $1.7 \times 10^{-8}$ | $>10^{-4}$ | $>10^{-4}$ | $>6,000$ |
| II | $1.2 \times 10^{-8}$ | $>10^{-4}$ | $3.0 \times 10^{-5}$ | 2,500 |
| III | $1.0 \times 10^{-8}$ | $>10^{-4}$ | $1.2 \times 10^{-5}$ | 1,200 |
| IV | $2.0 \times 10^{-7}$ | $>10^{-4}$ | $1.0 \times 10^{-4}$ | 500 |
| V | $6.2 \times 10^{-8}$ | $>10^{-4}$ | $4.0 \times 10^{-6}$ | 65 |
| VI | $3.0 \times 10^{-9}$ | $>10^{-4}$ | $9.5 \times 10^{-7}$ | 32 |
| VII | $3.0 \times 10^{-8}$ | | $>10^{-4}$ | 3,300 |
| VIII | | | | |
| IX | $1.0 \times 10^{-7}$ | $>10^{-4}$ | $1.7 \times 10^{-5}$ | 170 |
| X | $8.4 \times 10^{-9}$ | $>10^{-4}$ | $>10^{-4}$ | $>12,000$ |
| XI | $5.8 \times 10^{-8}$ | | $3.5 \times 10^{-5}$ | 600 |
| XII | $3.0 \times 10^{-10}$ | $>10^{-4}$ | $2.1 \times 10^{-5}$ | 70,000 |
| XIII | $1.0 \times 10^{-10}$ | $>10^{-4}$ | $8.4 \times 10^{-7}$ | 8,400 |
| XIV | $2.5 \times 10^{-9}$ | | $1.0 \times 10^{-6}$ | 400 |
| XV | $1.4 \times 10^{-11}$ | | $1.4 \times 10^{-5}$ | $10^6$ |
| XVI | | | | |
| XVII | $2.5 \times 10^{-10}$ | $>10^{-4}$ | $2.0 \times 10^{-6}$ | 8,000 |
| XVIII | $3.8 \times 10^{-10}$ | | $1.4 \times 10^{-6}$ | 3,700 |
| XIX | $1.2 \times 10^{-7}$ | | | |
| XX | $3.0 \times 10^{-9}$ | $>10^{-4}$ | $4.0 \times 10^{-5}$ | 13,000 |
| XXI | $1.1 \times 10^{-7}$ | | $>10^{-4}$ | $>900$ |
| XXII | $1.0 \times 10^{-9}$ | | $>10^{-4}$ | $>10^5$ |
| XXIII | $6.4 \times 10^{-8}$ | | $>10^{-4}$ | $>1,500$ |
| XXIV | $2.0 \times 10^{-7}$ | | $1.0 \times 10^{-4}$ | 500 |
| XXV | $2.6 \times 10^{-7}$ | | $3.7 \times 10^{-5}$ | 140 |
| XXVI | $6.5 \times 10^{-8}$ | $>10^{-4}$ | $1.0 \times 10^{-6}$ | 15 |
| XXVII | $2.0 \times 10^{-9}$ | $>10^{-4}$ | $>10^{-4}$ | $>50,000$ |
| XXVIII | $3.3 \times 10^{-8}$ | | | |
| XXIX | $1.4 \times 10^{-9}$ | | $>10^{-4}$ | $>70,000$ |
| XXX | $4.0 \times 10^{-9}$ | | $>10^{-4}$ | $>2,500$ |
| XXXI | $5.8 \times 10^{-11}$ | | $>10^{-4}$ | $>1.7 \times 10^6$ |
| XXXII | $3.6 \times 10^{-8}$ | | | |
| XXXIII | | | | |
| XXXIV | | | | |
| XXXV | $3.3 \times 10^{-9}$ | | $1.0 \times 10^{-6}$ | 300 |
| XXXVI | $1.1 \times 10^{-8}$ | | $1.0 \times 10^{-4}$ | 9,000 |
| XXXVII | $4.5 \times 10^{-8}$ | | $>10^{-4}$ | $>2,200$ |
| XXXVIII | $2.6 \times 10^{-8}$ | | $>10^{-4}$ | $>3,800$ |
| XXXIX | $8.6 \times 10^{-8}$ | | $1.8 \times 10^{-5}$ | 210 |
| XL | $2.0 \times 10^{-9}$ | $>10^{-4}$ | $1.7 \times 10^{-6}$ | 850 |
| XLI | $4.3 \times 10^{-9}$ | | | |
| XLII | $4.1 \times 10^{-10}$ | | $2.0 \times 10^{-5}$ | 49,000 |
| XLIII | $1.7 \times 10^{-9}$ | | $>10^{-4}$ | $>60,000$ |
| XLIV | | | | |
| XLV | $1.0 \times 10^{-7}$ | | | |
| XLVI | $1.2 \times 10^{-9}$ | | $6.8 \times 10^{-5}$ | 57,000 |
| XLVII | $2.3 \times 10^{-9}$ | | $8.0 \times 10^{-6}$ | 3,500 |
| XLVIII | | | | |
| XLIX | | | | |
| L | $6.6 \times 10^{-9}$ | $>10^{-4}$ | $3.0 \times 10^{-6}$ | 450 |

*Compound in which $R^1$, $R^2$, $R^3$ and $R^4$ are all hydrogen

The results given in the table show that all of the compounds tested caused a 50% inhibition of the thromboxane synthetase enzyme at a molar concentration level of as low as $2.6 \times 10^{-7}$ or even less, and that several of the compounds even caused 50% inhibition at concentrations of $10^{-9}$ or less. Of the compounds tested for inhibition of the cyclo-oxygenase enzyme, none cause 50% inhibition at a molar concentration level of $10^{-4}$ or less, so that their ability to inhibit that enzyme is at least 2,600 times less, and in some cases even 10,000 times less, than their ability to inhibit the thromboxane synthetase enzyme. Of the compounds tested for inhibition of the prostacyclin synthetase enzyme, none caused 50% inhibition at a molar concentration level of less than 15 times greater than that at which they caused 50% inhibition of the thromboxane synthetase enzyme, i.e., they were all at least 15 times more potent as inhibitors of the thromboxane synthetase enzyme than they were of prostacyclin synthetase. As a matter of fact, most of the compounds tested were at least 100 times more potent, while many were even 1,000 times and some were even 1,000,000 times more potent when examined in this connection.

What is claimed is:

1. A compound of the formula:

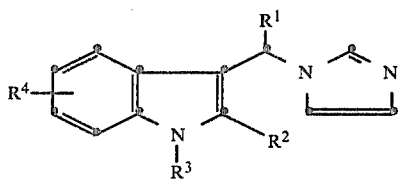

and the pharmaceutically acceptable acid addition salts thereof, wherein $R^1$ is hydrogen or lower alkyl;

$R^2$ is hydrogen, lower alkyl, lower cycloalkyl, adamantyl, or a phenyl or benzyl group in which the phenyl moiety is unsubstituted on the ring or is monosubstituted with halogen, hydroxy, lower alkyl, lower alkoxy or trifluoromethyl;

$R^3$ is hydrogen, lower alkyl, allyl, 3-methylallyl, lower cycloalkylmethyl, lower cycloalkylethyl, lower alkoxy-lower alkyl, di(lower alkyl)amino-lower alkyl, lower alkanoyl, lower cycloalkyl-carbonyl, or a benzyl or benzoyl group in which the phenyl moiety is unsubstituted on the ring or is monosubstituted with halogen, hydroxy, lower alkyl, lower alkoxy or trifluoromethyl; and $R^4$ is hydrogen, lower alkyl, lower alkoxy, halogen, hydroxy, trifluoromethyl, di(lower alkyl)amino, or a benzyloxy group in which the phenyl moiety is unsubstituted on the ring or is monosubstituted with halogen, hydroxy, lower alkyl, lower alkoxy or trifluoromethyl; with the proviso that at least one of $R^1$, $R^2$, $R^3$ and $R^4$ is other than hydrogen.

2. A compound as claimed in claim 1 wherein $R^1$ is hydrogen or methyl and $R^4$ is hydrogen.

3. A compound as claimed in claim 1 wherein $R^1$ is methyl, and $R^2$, $R^3$ and $R^4$ are each hydrogen.

4. A compound as claimed in claim 1 wherein $R^1$ is hydrogen, $R^2$ is lower alkyl and $R^3$ and $R^4$ are each hydrogen.

5. A compound as claimed in claim 1 wherein $R^1$ is hydrogen, $R^2$ is lower cycloalkyl and $R^3$ and $R^4$ are each hydrogen.

6. A compound as claimed in claim 1 wherein $R^1$ is hydrogen, $R^2$ is benzyl and $R^3$ and $R^4$ are each hydrogen.

7. A compound as claimed in claim 1 wherein $R^1$ is hydrogen, $R^2$ is halophenyl and $R^3$ and $R^4$ are each hydrogen.

8. A compound as claimed in claim 1 wherein $R^1$ is hydrogen, $R^2$ is tolyl and $R^3$ and $R^4$ are each hydrogen.

9. A compound as claimed in claim 4 wherein $R^2$ is isopropyl.

10. A compound as claimed in claim 5 wherein $R^2$ is cyclopropyl.

11. A compound as claimed is claim 5 wherein $R^2$ is cyclohexyl.

12. A compound as claimed in claim 7 wherein $R^2$ is o-chlorophenyl.

13. A compound as claimed in claim 1 wherein $R^1$ is hydrogen or methyl, $R^2$ is hydrogen, $R^3$ is lower alkyl and $R^4$ is hydrogen.

14. A compound as claimed in claim 1 wherein $R^1$ is hydrogen or methyl, $R^2$ is hydrogen, $R^3$ is allyl and $R^4$ is hydrogen.

15. A compound as claimed in claim 1 wherein $R^1$ and $R^2$ are each hydrogen, $R^3$ is lower cycloalkylmethyl and $R^4$ is hydrogen.

16. A compound as claimed in claim 1 wherein $R^1$ and $R^2$ are each hydrogen, $R^3$ is lower alkanoyl and $R^4$ is hydrogen.

17. A compound as claimed in claim 1 wherein $R^1$ and $R^2$ are each hydrogen, $R^3$ is p-methylbenzoyl and $R^4$ is hydrogen.

18. A compound as claimed in claim 1 wherein $R^1$ and $R^2$ are each hydrogen, $R^3$ is p-methoxybenzoyl and $R^4$ is hydrogen.

19. A compound as claimed in claim 13 wherein $R^3$ is methyl.

20. A compound as claimed in claim 13 wherein $R^3$ is ethyl.

21. A compound as claimed in claim 13 wherein $R^3$ is n-propyl.

22. A compound as claimed in claim 15 wherein $R^3$ is cyclopropylmethyl.

23. A compound as claimed in claim 16 wherein $R^3$ is acetyl.

24. A pharmaceutical composition useful for inhibiting the action of the thromboxane synthetase enzyme in an animal without significantly inhibiting the action of the prostacyclin synthetase or cyclo-oxygenase enzymes, said composition being in dosage unit form and comprising a pharmaceutically acceptable carrier and a thromboxane synthetase enzyme inhibiting amount of a compound selected from the group consisting of 3-(imidazol-1-ylalkyl) indoles of the formula:

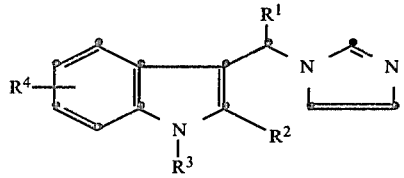

and the pharmaceutically acceptable acid addition salts thereof, wherein $R^1$ is hydrogen or lower alkyl $R^2$ is hydrogen, lower alkyl, lower cycloalkyl, adamantyl, or a phenyl or benzyl group in which the phenyl moiety is unsubstituted on the ring or is monosubstituted with halogen, hydroxy, lower alkyl, lower alkoxy or trifluoromethyl;

$R^3$ is hydrogen, lower alkyl, allyl, 3-methylallyl, lower cycloalkylmethyl, lower cycloalkylethyl, lower alkoxy-lower alkyl, di(lower alkyl) amino-lower alkyl, lower alkanoyl, lower cycloalkylcarbonyl, or a benzyl or benzoyl group in which the phenyl moiety is unsubstituted on the ring or is monosubstituted with halogen, hydroxy, lower alkyl, lower alkoxy or trifluoromethyl; and $R^4$ is hydrogen, lower alkyl, lower alkoxy, halogen, hydroxy, trifluoromethyl, di(lower alkyl) amino, or a benzyloxy group in which the phenyl moiety is unsubstituted on the ring or is monosubstituted with halogen, hydroxy, lower alkyl, lower alkoxy or trifluoromethyl; with the proviso that at least one of $R^1$, $R^2$, $R^3$ and $R^4$ is other than hydrogen.

25. The composition according to claim 24 wherein the compound is 3-(imidazol-1-ylmethyl)-2-isopropylindole.

26. The composition according to claim 24 wherein the compound is 3-(imidazol-1-ylmethyl)-1-methylindole.

27. A method of inhibiting the action of the thromboxane synthetase enzyme in an animal without significantly inhibiting the action of the prostacyclin synthetase or cyclo-oxygenase enzymes which comprises administering to said animal a thromboxane synthetase enzyme inhibiting amount of a compound of the formula

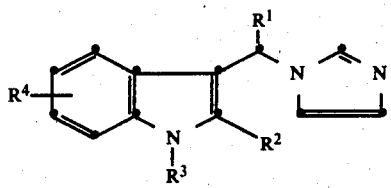

or a pharmaceutically acceptable acid addition salt thereof, wherein $R^1$ is hydrogen or lower alkyl;

$R^2$ is hydrogen, lower alkyl, lower cycloalkyl, adamantyl, or a phenyl or benzyl group in which the phenyl moiety is unsubstituted on the ring or is monosubstituted with halogen, hydroxy, lower alkyl, lower alkoxy or trifluoromethyl;

$R^3$ is hydrogen, lower alkyl, allyl, 3-methylallyl, lower cycloalkylmethyl, lower cycloalkylethyl, lower alkoxylower alkyl, di(lower alkyl) aminolower alkyl, lower alkanoyl, lower cycloalkyl-carbonyl, or a benzyl or benzoyl group in which the phenyl moiety is unsubstituted on the ring or is monosubstituted with halogen, hydroxy, lower alkyl, lower alkoxy or trifluoromethyl; and $R^4$ is hydrogen, lower alkyl, lower alkoxy, halogen hydroxy, trifluoromethyl, di(lower alkyl) amino, or a benzyloxy group in which the phenyl moiety is unsubstituted on the ring or is monosubstituted with halogen, hydroxy, lower alkyl, lower alkoxy or trifluoromethyl.

28. The method of claim 27 wherein said compound is 3-(imidazol-1-ylmethyl) indole.

29. The method of claim 27 wherein said compound is 3-(imidazol-1-ylmethyl)-2-isopropylindole.

30. The method of claim 27 wherein said compound is 3-(imidazol-1-ylmethyl)-1-methylindole.